(12) United States Patent
Hamada et al.

(10) Patent No.: US 10,765,663 B2
(45) Date of Patent: Sep. 8, 2020

(54) NUTRITION COMPOSITION

(71) Applicant: AJINOMOTO CO., INC., Tokyo (JP)

(72) Inventors: Mika Hamada, Kanagawa (JP); Kenji Nagao, Kanagawa (JP); Asuka Seki, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/834,880

(22) Filed: Aug. 25, 2015

(65) Prior Publication Data

US 2015/0359252 A1 Dec. 17, 2015

Related U.S. Application Data

(63) Continuation of application No. PCT/JP2014/054644, filed on Feb. 26, 2014.

(30) Foreign Application Priority Data

Feb. 26, 2013 (JP) ................................. 2013-036436

(51) Int. Cl.
| | |
|---|---|
| A61K 31/405 | (2006.01) |
| A23L 33/00 | (2016.01) |
| A23L 33/175 | (2016.01) |
| A23L 2/52 | (2006.01) |
| A23L 2/66 | (2006.01) |
| A61K 31/198 | (2006.01) |

(52) U.S. Cl.
CPC .............. *A61K 31/405* (2013.01); *A23L 2/52* (2013.01); *A23L 2/66* (2013.01); *A23L 33/175* (2016.08); *A23L 33/30* (2016.08); *A61K 31/198* (2013.01); *A23V 2002/00* (2013.01)

(58) Field of Classification Search
CPC .................................................. A61K 31/405
See application file for complete search history.

(56) References Cited

U.S. PATENT DOCUMENTS

| | | | | |
|---|---|---|---|---|
| 3,697,287 | A | * | 10/1972 | Winitz .................. A23L 33/175 426/648 |
| 4,009,265 | A | | 2/1977 | Howard |
| 4,900,566 | A | | 2/1990 | Howard |
| 5,132,113 | A | | 7/1992 | Luca |
| 5,242,697 | A | * | 9/1993 | Luca ...................... A61K 31/70 426/231 |
| 5,728,678 | A | | 3/1998 | Trimbo et al. |
| 6,077,828 | A | | 6/2000 | Abbruzzese et al. |
| 6,326,355 | B1 | | 12/2001 | Abbruzzese et al. |
| 6,387,883 | B1 | | 5/2002 | Abbruzzese et al. |
| 2002/0099020 | A1 | | 7/2002 | Abbruzzese et al. |
| 2004/0087490 | A1 | | 5/2004 | Troup et al. |
| 2004/0167081 | A1 | | 8/2004 | Abbruzzese et al. |
| 2004/0171690 | A1 | | 9/2004 | Ammann et al. |
| 2007/0196445 | A1 | | 8/2007 | Abbruzzese et al. |
| 2009/0012168 | A1 | | 1/2009 | Maezono et al. |
| 2013/0090297 | A1 | | 4/2013 | Troup et al. |

FOREIGN PATENT DOCUMENTS

| | | | |
|---|---|---|---|
| EP | 1121865 | A2 | 8/2001 |
| JP | 63-502558 | A | 9/1988 |
| JP | 04-346770 | A | 12/1992 |
| JP | 6-24977 | A | 2/1994 |
| JP | 09-020678 | A | 1/1997 |
| JP | 09-052828 | A | 2/1997 |
| JP | 09-157163 | A | 6/1997 |
| JP | 10-028553 | A | 2/1998 |
| JP | 11-508282 | A | 7/1999 |
| JP | 2005-505500 | A | 2/2005 |
| JP | 2006-022072 | A | 1/2006 |
| JP | 2007-197363 | A | 8/2007 |
| WO | WO2004/026294 | A1 | 4/2004 |
| WO | WO2006/070873 | A1 | 7/2006 |
| WO | WO 2009143937 | A1 * | 12/2009 ............. A23L 1/034 |

OTHER PUBLICATIONS

Valerio et al., Branched-chain amino acids, mitochondrial biogenesis, and healthspan: an evolutionary perspective., 2011, Aging, vol. 3, No. 5, pp. 464-478.*
Search Report for European Patent App. No. 14757392.7 (dated Jul. 6, 2016).
English language International Preliminary Report on Patentability for PCT Patent App. No. PCT/JP2014/054644 (dated Sep. 1, 2015).
Acar., N., et al., "Appetite Suppressant Activity of Supplemental Dietary Amino Acids and Subsequent Compensatory Growth of Broilers," Poult. Sci. 2001;80(8):1215-1222 Abstract, Figure 1.
Marx, J., "Cellular Warriors at the Battle of the Bulge," Science 2003;299(5608):846-849.
Edmonds, M. S., et al., "Amino Acid Excesses for Young Pigs: Effects of Excess Methionine, Tryptophan, Threonine or Leucine," J. Anim. Sci. 1987;64:1664-1671.
English translation of Notification of Reasons for Refusal from Japanese Patent App. No. 2015-502946 (dated Mar. 6, 2018).
Thomas, D. R., "Use of Orexigenic Medications in Geriatric Patients," Am. J. Geriatric Pharmacotherapy, Excerpta Medica, 2011, vol. 9, No. 2, pp. 97-108.
Communication Pursuant to Article 94(3) EPC from European Patent App. No. 14757392.7 (Jul. 8, 2020).

* cited by examiner

*Primary Examiner* — Kortney L. Klinkel
*Assistant Examiner* — Tori Strong
(74) *Attorney, Agent, or Firm* — Cermak Nakajima & McGowan LLP; Shelly Guest Cermak

(57) ABSTRACT

The present invention provides a food intake regulating agent which improves anorexia and overeating and is safe for ingestion for a long term. The present invention relates to a food intake regulating agent containing 3 kinds of amino acids: threonine, methionine and tryptophan, as active ingredients.

14 Claims, 5 Drawing Sheets

NUTRITION COMPOSITION

This application is a continuation of International Patent Application No. PCT/JP2014/054644, filed on Feb. 26, 2014, and claims priority to Japanese Patent Application No. 2013-036436, filed on Feb. 26, 2013, all of which are incorporated herein by reference in their entireties.

BACKGROUND OF THE INVENTION

Field of the Invention

The present invention relates to a food intake regulating agent containing 3 kinds of amino acids: threonine, methionine and tryptophan. More particularly, the present invention relates to a food intake regulating agent useful for the prophylaxis or improvement of undernutrition due to decreased appetite, lifestyle-related diseases due to overeating and the like.

Brief Description of the Related Art

In the body, information is collected in the brain through various hormones, cytokines, low molecules, neural connection and the like, and homeostasis is maintained by 1. enhancing or decreasing the appetite over a long term or short term
2. changing the state of metabolism
3. changing the amount of motor activity
(See Science 2003 Vol. 299, No. 5608, pp. 846-849).

It is also known that people gain or lose weight based on the balance between intake calorie from food and calorie consumption by basal metabolism and exercise.

Obesity is developed by a disturbed balance of the above-mentioned homeostasis and calorie consumption, and produces many patients with lifestyle-related diseases such as hypertension, diabetes, hyperlipidemia and the like and people at risk thereof. Food consumption is increasing on a global scale, the obese individuals are still increasing, and prophylaxis or improvement of obesity has been desired.

As a substance that regulates, particularly suppresses, food intake, mazindol in amphetamines is put to practical use as a pharmaceutical product. However, the use thereof is limited to highly obese individuals in view of the direct action of mazindol on the central nervous system and the risk of addiction, dependency and the like. Thus, a safe product that suppresses overeating and prevents obesity has been desired.

On the other hand, elderly people have difficulty in maintaining homeostasis and fall in an undernutrition state due to, for example, a decrease in digestion ability, chewing ability, swallowing ability, exercise capacity, sense of taste, sense of smell and vision, low appetite resulting from change of preference and unbalanced diet because of an influence of disease and drugs. Consequently, they cannot lead a comfortable daily life and suffer from low quality of life (hereinafter to be referred to as QOL) of patients, thus posing a problem.

In addition, cancer patients, patients in an undernutrition state from anorexia due to the side effects of anti-cancer agents and the like, who cannot ingest sufficient nutrition, patients showing insufficient oral ingestion due to anorexia and stress caused by a disease and the like, the above-mentioned elderly people with unsatisfactory nutrition condition and the like may fall under Protein-Energy Malnutrition (PEM) which is undernutrition associated with lack of energy, thus problematically progressing into exacerbated nutrition conditions. However, an effective treatment method has not been established.

As a method for the prophylaxis or treatment of cachexia and anorexia, use of branched chain amino acids such as valine and isoleucine and a small amount of tryptophan is described. However, simultaneous use of antioxidant components such as ω-6 fatty acid, ω-3 fatty acid, β-carotene and the like is essential (See JP-A-11-508282).

There is no report on the improvement of anorexia by free amino acid alone, particularly methionine or threonine, as an essential component.

An appetite control agent containing St. John's wort and an amino acid composed of at least one kind from tryptophan, phenylalanine, arginine, glutamine, histidine, methionine and tyrosine is described (See JP-A-2006-22072).

However, there is no report on the suppression of appetite by a free amino acid alone, particularly threonine as an essential component.

SUMMARY OF THE INVENTION

The present invention aims to provide a food intake regulating agent which improves anorexia and overeating and is safe for ingestion for a long term.

The present inventors have conducted intensive studies in view of the above-mentioned problems and found that a composition containing threonine, methionine and tryptophan, and the composition further containing isoleucine and/or valine have a food intake promoting action and a food intake suppressive action in combination, and can regulate food intake.

It is an aspect of the present invention to provide a composition which is able to regulate food intake in a subject comprising tryptophan, threonine and methionine.

It is a further aspect of the present invention to provide the composition as described above, wherein the weight ratio of tryptophan, threonine and methionine is 1:0.5-12:0.2-10.

It is a further aspect of the present invention to provide the composition as described above, further comprising isoleucine.

It is a further aspect of the present invention to provide the composition as described above, wherein the weight ratio of tryptophan, threonine, methionine and isoleucine is 1:0.5-12:0.2-10:0.5-12.

It is a further aspect of the present invention to provide the composition as described above, further comprising valine.

It is a further aspect of the present invention to provide the composition as described above, wherein the weight ratio of tryptophan, threonine, methionine, isoleucine and valine is 1:0.5-12:0.2-10:0.5-12:0.5-15.

It is a further aspect of the present invention to provide the composition as described above, which is in a unit packaging form for one meal and comprises, in the unit, not less than 0.06 g of amino acid as an amount to be ingested for one meal as an active ingredient.

It is a further aspect of the present invention to provide the composition as described above, which is for the prophylaxis or improvement of reduction in appetite or an undernutrition state due to reduction in appetite.

It is a further aspect of the present invention to provide the composition as described above, wherein the reduction in appetite is caused by one or more kinds selected from aging, cancer, inflammation, decreased function of digestive organ, cardiac failure, renopathy, hepatic diseases, autoimmune disorder, lung disease, hypothyroidism, encephalopathy, anorexia nervosa, depression, dementia, Alzheimer's disease, chemotherapeutic agent, antibiotic, therapeutic agent for diabetes, trauma after surgery, lack of ghrelin secretion, lack of ghrelin action, psychological stress, physical stress, irregular lifestyle habit, unbalanced diet and low-protein diet.

It is a further aspect of the present invention to provide the composition as described above, which is for the prophylaxis or improvement of overeating or a lifestyle-related disease caused by overeating.

It is a further aspect of the present invention to provide the composition as described above, wherein the overeating is caused by psychological stress, physical stress, bulimia nervosa, depression, irregular lifestyle habit or low-protein diet.

It is a further aspect of the present invention to provide a food or drink for regulating food intake, which is in a unit packaging form for one meal, and comprises not less than 0.06 g in total of 3 kinds of amino acids of tryptophan, threonine and methionine in the unit, wherein the weight ratio of tryptophan, threonine and methionine is 1:0.5-12:0.2-10.

It is a further aspect of the present invention to provide the food or drink as described above, which is free of an amino acid other than tryptophan, threonine and methionine.

It is a further aspect of the present invention to provide the food or drink as described above, which is in a unit packaging form for one meal, and comprises not less than 0.06 g in total of 4 kinds of amino acids of tryptophan, threonine, methionine and isoleucine in the unit, wherein the weight ratio of tryptophan, threonine, methionine and isoleucine is 1:0.5-12:0.2-10:0.5-12.

It is a further aspect of the present invention to provide the food or drink as described above, which is free of an amino acid other than tryptophan, threonine, methionine and isoleucine.

It is a further aspect of the present invention to provide the food or drink as described above, which is in a unit packaging form for one meal, and comprises not less than 0.06 g in total of 5 kinds of amino acids of tryptophan, threonine, methionine, isoleucine and valine in the unit, wherein the weight ratio of tryptophan, threonine, methionine, isoleucine and valine is 1:0.5-12:0.2-10:0.5-12:0.5-15.

It is a further aspect of the present invention to provide the food or drink as described above, which is free of an amino acid other than tryptophan, threonine, methionine, isoleucine and valine.

According to the present invention, the body can be maintained in a normal state by controlling food intake by decreasing or promoting appetite according to the condition of the body by only ingesting at least 3 kinds of amino acids of tryptophan, threonine and methionine. In addition, since amino acids are the active ingredients, food intake can be safely regulated by administration thereof for a long term; obesity and undernutrition can be improved; and QOL can be increased.

According to the present invention, moreover, food ingestion frequency and amount thereof particularly in elderly people can be improved to increase the ingestion amounts of energy, protein, lipid, vitamin and the like. Of these, ingestion of the food in the first group (fish, meat, egg, bean, soybean product etc.) in the six basic foods increases, and the body weight can be increased.

DETAILED DESCRIPTION OF THE PREFERRED EMBODIMENTS

Figure 1:
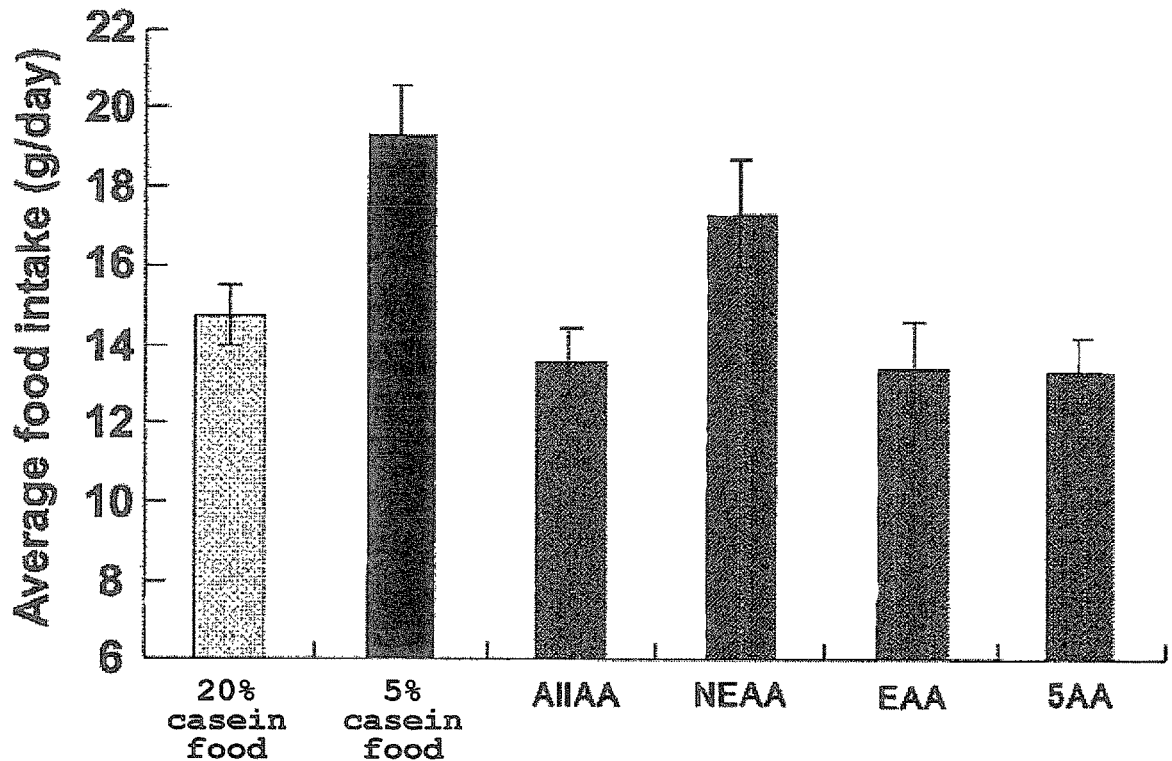
FIG. 1 shows an average food intake per day at 2 weeks after feed exchange.

The present invention relates to a food intake regulating agent comprising at least 3 kinds of amino acids: (1) tryptophan, (2) threonine and (3) methionine.

The food intake regulating agent of the present invention may further contain 4 or 5 kinds including (4) isoleucine or (4) isoleucine and (5) valine. Particularly, 5 kinds of amino acids of tryptophan, threonine, methionine, isoleucine and valine are preferably contained as active ingredients (hereinafter food intake regulating agents containing (1)-(3), (1)-(4) or (1)-(5) as active ingredients are sometimes to be generically abbreviated as the food intake regulating agent of the present invention).

The amino acids of the above-mentioned (1)-(5) to be used in the present invention may be any of an L-form, a D-form and a DL-form, with preference given to L-form.

The amino acids of the above-mentioned (1)-(5) to be used in the present invention may be in the form of a salt, and the amino acid is a concept also including a salt.

Examples of the salt of the amino acids of (1)-(5) include acid addition salt, metal salt, ammonium salt, organic amine addition salt, amino acid addition salt and the like.

Examples of the acid addition salt include inorganic acid salts such as hydrochloride, sulfate, nitrate, phosphate and the like, organic acid salts such as acetate, maleate, fumarate, citrate, malate, lactate, α-ketoglutarate, gluconate, caprylate and the like.

Examples of the metal salt include alkali metal salts such as sodium salt, potassium salt and the like, alkaline earth metal salts such as magnesium salt, calcium salt and the like, aluminum salt, zinc salt and the like.

Examples of the ammonium salt include salts such as ammonium, tetramethylammonium and the like.

Examples of the organic amine addition salt include salts with morpholine, piperidine and the like.

Examples of the amino acid addition salt include salts with glycine, phenylalanine, lysine, aspartic acid, glutamic acid and the like.

The salt of the amino acids of (1)-(5) may be a hydrate (hydrate salt), and examples of the hydrate include 1-6 hydrates and the like.

The amino acids of (1)-(5) of the present invention may be produced by any production method such as protein hydrolysis method, chemical synthesis method, enzyme method, fermentation method and the like, or commercially available products can also be used.

The amino acids of (1)-(5) of the present invention can also be obtained by enzymatically hydrolyzing natural proteins having the amino acid sequence thereof.

In the present invention, the "regulation of food intake" means regulation of food intake by enhancing or decreasing the appetite for a long or short term. That is, it is a concept encompassing maintaining the body in a healthy condition by promotion or suppression of food intake by enhancing the appetite of a subject or a target animal having a reduced appetite and decreasing the appetite of a subject and the like showing an enhanced appetite.

To maintain the body in a healthy condition means to maintain the ideal body weight, and the ideal body weight of human can be judged based on, for example, BMI (Body Mass Index) as an index.

$$BMI = \text{body weight (kg)} \div \text{body height (m)} \div \text{body height (m)}$$

less than 18.5 thin
18.5—less than 25 normal
25—obese

Promotion of food intake is a concept encompassing bringing decreased amounts of meal and feed or intake calorie to normal values, and further, increasing the values to a level suitable for curing the disease.

Suppression of food intake is a concept encompassing bringing excess amounts of meal and feed or intake calorie to normal values, and further, decreasing the values to a level suitable for curing the disease.

As used herein, the normal value is determined based on the age, sex, body height, basal metabolism, amount of motor activity and the like. For example, the above-mentioned amounts of meal and feed or intake calorie capable of maintaining the ideal body weight are considered to be normal values.

The food intake regulating agent of the present invention can enhance food intake and is used as a food intake enhancer, and is effective for the prophylaxis or improvement of reduction of appetite and undernutrition due to reduction of appetite.

As used herein, the improvement is a concept encompassing bringing a decreased appetite and undernutrition to a normal level, and further, prevention of progression (exacerbation) of diseases.

Examples of the reduction of appetite include reduction of appetite due to aging, cancer, inflammation, decreased function of digestive organ, cardiac failure, renopathy, hepatic disease, autoimmune disorder, lung disease, hypothyroidism, encephalopathy, anorexia nervosa, depression, dementia, Alzheimer's disease, drug administration of anti-cancer agent, chemotherapeutic agent, antibiotic, therapeutic agent for diabetes and the like, and reduction of appetite in the subjects and target animals affected with trauma after surgery and the like.

Also, reduction of appetite due to insufficient secretion of ghrelin which is a food intake promoting peptide produced in the periphery and having an important action on the regulation of energy metabolism such as promotion of food intake, body weight increase, regulation of gastrointestinal function and the like and insufficient action of ghrelin can be mentioned.

In addition, reduction of appetite due to low-protein diet, reduction of appetite due to psychological or physical stress, reduction of appetite due to irregular lifestyle habit, reduction of appetite due to unbalanced diet and the like can be mentioned.

The food intake regulating agent of the present invention is also preferably used for undernutrition, particularly Protein-Energy Malnutrition (PEM) caused by lack of protein and lack of energy occurring in combination. Specifically, "undernutrition" refers to a state where nutrients in amounts necessary for a healthy life have not been ingested.

The food intake regulating agent of the present invention is preferably used for reduction of appetite due to aging (reduction of appetite in elderly people), reduction of appetite in cancer patients, reduction of appetite due to anti-cancer agent treatment, reduction of appetite due to lack of ghrelin secretion or lack of ghrelin action, reduction of appetite due to low-protein diet and reduction of appetite due to undernutrition resulting therefrom.

Reduction of appetite due to aging means a decrease in the frequency and amount of food intake.

The food intake regulating agent of the present invention is also preferably used for body weight decrease due to the above-mentioned reduction of appetite.

When the food intake regulating agent of the present invention is used as a food intake enhancing agent, at least the amino acids (1)-(3) of the present invention need to be contained, and the amino acids of (1)-(4) or (1)-(5) are preferably contained.

The food intake regulating agent of the present invention can suppress food intake and used as a food intake inhibitor. It is effective for the prophylaxis or improvement of overeating and lifestyle-related diseases due to overeating.

As used herein, improvement is a concept encompassing bringing promoted appetite and overeating to a normal level, and further, preventing progression (exacerbation) of diseases.

Examples of the overeating include psychological stress, physical stress, low-protein diet, bulimia nervosa, depression, and overeating due to irregular lifestyle habit.

Examples of the lifestyle-related disease due to overeating include metabolic syndrome, obesity, visceral fat accumulation, hypertension, hyperlipidemia, diabetes, impaired glucose tolerance, alcoholic fatty liver, non-alcoholic fatty liver, non-alcoholic steatohepatitis, hyperuricemia, coronary heart disease, cerebral apoplexy and the like. Of these, metabolic syndrome, obesity, hypertension, hyperlipidemia, diabetes and the like are effective.

When the food intake regulating agent of the present invention is used as a food intake inhibitor, at least the amino acids (1)-(3) of the present invention need to be contained, and the amino acid of (4) or (5) or (4) and (5) are preferably contained.

The food intake regulating agent of the present invention means pharmaceutical products used for "regulating food intake", a composition similar to a pharmaceutical product or functional food having a particular function and taken for the purpose of maintaining health and the like, such as health supplements, foods with health claims, supplements and the like.

The food intake regulating agent of the present invention can be applied to human, animals other than human [for example, mammals other than human (domestic animals and pet animals such as swine, bovine, horse, canine and the like), birds (poultry and pet animals such as turkey, chicken and the like)] and the like.

In the food intake regulating agent of the present invention, the weight ratio of tryptophan, threonine and methionine is generally 1:0.5-12:0.2-10, preferably 1:1-9:0.5-8, more preferably 1:2-6:1-5.

In the food intake regulating agent of the present invention, the weight ratio of tryptophan, threonine, methionine and isoleucine is generally 1:0.5-12:0.2-10:0.5-12, preferably 1:1-9:0.5-8:1-9, more preferably 1:2-6:1-5:2-6.

In the food intake regulating agent of the present invention, the weight ratio of tryptophan, threonine, methionine, isoleucine and valine is generally 1:0.5-12:0.2-10:0.5-12:0.5-15, preferably 1:1-9:0.5-8:1-9:1.5-10, more preferably 1:2-6:1-5:2-6:3-7.

The content of each amino acid in the food intake regulating agent of the present invention is as follows.

In the food intake regulating agent containing the amino acids of (1)-(3) of the present invention, the weight (%) of each amino acid in the containing amino acids is
i. tryptophan 0.5%-45%, (2) threonine 1.5%-70%, (3) methionine 1.0%-50%, preferably (1) 3.5%-40%, (2) 5%-65%, (3) 6%-45%, more preferably (1) 5%-33%, (2) 8%-60%, (3) 10%-40%.

In the food intake regulating agent containing the amino acids of (1)-(4) of the present invention, the weight (%) of each amino acid in the contained amino acids is
ii. tryptophan 0.5%-45%, (2) threonine 1.5%-70%, (3) methionine 1.0%-50%, (4) isoleucine 0.001%-50%, preferably (1) 3.5%-40%, (2) 5%-65%, (3) 6%-45%, (4) 0.001%-45%, more preferably (1) 5%-33%, (2) 8%-60%, (3) 10%-40%, (4) 0.001%-40%.

In the food intake regulating agent containing the amino acids of (1)-(5) of the present invention, the weight (%) of each amino acid in the contained amino acids is
iii. tryptophan 0.5%-45%, (2) threonine 1.5%-70%, (3) methionine 1.0%-50%, (4) isoleucine 0.001%-50%, (5) valine 0.001%-60%, preferably (1) 3.5%-40%, (2) 5%-65%, (3) 6%-45%, (4) 0.001%-45%, (5) 0.001%-55%, more preferably (1) 5%-33%, (2) 8%-60%, (3) 10%-40%, (4) 0.001%-40%, (5) 0.001%-50%.

As used herein, the contained amino acid means a free amino acid, and does not include constituent amino acids in protein and peptide.

While the dose of the food intake regulating agent of the present invention varies depending on the age, sex, body weight, target disease, symptom, and dosage form, it is generally within the range of 60 mg-23 g, preferably 100 mg-20 g, more preferably 500 mg-15 g, further preferably 500 mg-5 g, particularly preferably 500 mg-2 g, in total of the amino acids of (1)-(3) for an adult (e.g., body weight 60 kg) per day, which is administered once to several times a day.

Similarly, the dose of the food intake regulating agent of the present invention is generally within the range of 60 mg-23 g, preferably 100 mg-20 g, more preferably 500 mg-15 g, further preferably 500 mg-5 g, particularly preferably 500 mg-2 g, in total of the amino acids of (1)-(4) for an adult per day, which is administered once to several times a day.

Similarly, the dose of the food intake regulating agent of the present invention is generally within the range of 60 mg-23 g, preferably 100 mg-20 g, more preferably 500 mg-15 g, further preferably 500 mg-5 g, particularly preferably 500 mg-2 g, in total of the amino acids of (1)-(5) for an adult per day, which is administered once to several times a day.

The dose of (1) is generally within the range of 10 mg-9 g, preferably 20 mg-6 g, more preferably 80 mg-5 g, for an adult per day. A range of 90 mg-1 g is particularly preferable.

The dose of (2) is generally within the range of 30 mg-20 g, preferably 60 mg-18 g, more preferably 250 mg-15 g, for an adult per day. A range of 250 mg-1 g is particularly preferable.

The dose of (3) is generally within the range of 20 mg-18 g, preferably 40 mg-15 g, more preferably 170 mg-12 g, for an adult per day. A range of 180 mg-1 g is particularly preferable.

The dose of (4) is generally within the range of 0 mg-20 g, preferably 60 mg-18 g, more preferably 250 mg-15 g, for an adult per day. A range of 300 mg-1 g is particularly preferable.

The dose of (5) is generally within the range of 0 mg-20 g, preferably 100 mg-18 g, more preferably 300 mg-18 g, further preferably 400 mg-16 g, for an adult per day. A range of 500 mg-1 g is particularly preferable.

The above-mentioned amount for an adult per one time can be appropriately changed in consideration of the body conditions such as sex, age, disease and the like.

Using the food intake regulating agent of the present invention, the above-mentioned amount per day can be administered once or divided in several portions. The dosing period is not particularly limited, and the agent can be administered for a long term since the ingredient is derived from amino acid.

The food intake regulating agent of the present invention is not particularly limited as to the dosage form thereof, and may be any of an oral preparation and a parenteral preparation. The dosage form thereof may be oral agents such as tablet, granule, powder, capsule, elixir, syrup, microcapsule, drink, emulsion, suspension and the like, external skin agents such as ointment, cream, gel, liquid, lotion, mask, bath additive and the like, injection and the like.

For oral administration, the food intake regulating agent of the present invention can contain carrier, excipient, binder, swelling agent, lubricant, sweetening agent, flavor, preservative, emulsifier, coating agent and the like as necessary, and can be used together with these in a unit dose form required for generally-recognized formulation practice. The amount of the amino acid in these compositions and preparations may be an amount affording a suitable dose within the indicated range.

Specific examples of the component that can be contained in the food intake regulating agent of the present invention include binders such as tragacanth, gum arabic, cornstarch and gelatin, polymerpolyvinylpyrrolidone and the like; excipients such as cellulose (microcrystalline cellulose, crystalline cellulose, hydroxypropylcellulose and the like) and a derivative thereof; swelling agents such as cornstarch, pregelatinized starch, alginic acid, and dextrin; lubricants such as magnesium stearate; flowability improver such as fine silicon dioxide, and methylcellulose; lubricants such as glycerol acid ester, talc, polyethylene glycol 6000 and the like; thickeners such as sodium carboxymethylcellulose, carboxyvinyl polymer, xanthan gum, gelatin and the like; sweetening agents such as sucrose, lactose and aspartam; flavors such as peppermint, vanilla flavor and cherry or orange; emulsifiers such as monoglyceride, polyglycerol ester of fatty acid, sucrose fatty acid ester, lecithin, polyoxyethylene hydrogenated castor oil, polyoxyethylenemonostearic acid ester and the like; pH adjusters such as citric acid, sodium citrate, acetic acid, sodium acetate, sodium hydroxide and the like; corrigents such as aspartame, licorice extract, saccharin and the like; antioxidants such as erythorbic acid, butylhydroxyanisole, propyl gallate and the like; preservatives such as sodium benzoate, sodium edetate, sorbic acid, sodium sorbate, methyl p-hydroxybenzoate, butyl p-hydroxybenzoate and the like, colorants such as ferric oxide red, yellow iron oxide, black iron oxide, carnine, Food Color blue No. 1, Food Color Yellow No. 4, Food Color Red No. 2 and the like, and the like.

When the dosage unit form is a capsule, a liquid carrier such as fats and oils can be further added to the above-mentioned type of materials.

Various other materials can also be contained to change the physical form of the dosage unit. Examples of the coating agent for tablet include shellac, sugar or the both and the like. Syrup and elixir can contain, for example, sucrose as sweetening agent, methylparaben and propylparaben as preservative, dye, cherry or orange flavor and the like, and the like. Other various vitamins, and various amino acids may be contained.

For an enteric preparation, for example, an aqueous solution of hydroxylphenylmethylcellulose is used as a coating pre-treatment agent, and an aqueous solution of hydroxypropylmethylcellulosephthalate and an aqueous solution of polyacetin are used as coating agents to produce an enteric preparation according to a conventional method.

The food intake regulating agent of the present invention contains at least the amino acids of (1)-(3) as active ingredients, and may further contain other optional active ingredient and other amino acid. As other amino acid, isoleucine or valine is preferable, but other amino acid may also be used. When other amino acid is other than isoleucine and valine, the content of other amino acid is preferably not more than 60 wt %, more preferably not more than 40 wt %, further preferably not more than 20 wt %, of the contained amino acids.

For parenteral administration, for example, a solution containing the amino acids of (1)-(3) can be sprayed nasally, administered as an injection and the like. Alternatively, when the food intake regulating agent of the present invention is an external skin preparation, the amino acids of (1)-(3) may be dispersed in various bases and formulated according to a conventional method. Examples of such base include higher fatty acid esters such as petrolatum, liquid paraffin, isopropyl myristate, octyldodecyl myristate and the like, higher alcohols such as squalane, lanolin, cetanol and the like, oleaginous bases such as silicone oil, fats and oils of animals and plants and the like, lower alcohols such as ethanol and the like, polyvalent alcohols such as polyethylene glycol, propylene glycol and the like. Additives such as emulsifier and emulsion stabilizers such as α-monoglycerylether, lecithin, sorbitan fatty acid ester, dextrin fatty acid ester, fatty acid monoglyceride, fatty acid metal salt, magnesium sulfate and the like, aromatic, preservative, dye, thickener, antioxidant, UV protective agent, various efficacy agents such as wound healing agent, anti-inflammatory agent, moisturizer and the like and water may be added.

The pharmaceutical product in the present invention may be the food intake regulating agent itself of the present invention, or may also contain other additive and the like.

When the food intake regulating agent of the present invention is used as a food, it means a health food ingested by taking note of the particular function of the present invention, as well as a food for specified health uses and a food with nutrient function claims as defined in the food with health claims system, and further includes dietary supplements. While the amount of the amino acid contained in a food is not particularly limited, the amount to be drunk or eaten per day is preferably set to fall within a range similar to that of the above-mentioned dose of the food intake regulating agent of the present invention. The form of the food intake regulating agent of the present invention as a food with health claims is not particularly limited.

The food in the present invention may be in a unit intake form for one meal containing the amino acids of (1)-(3), (1)-(4) or (1)-(5) and the like, the form of a bottle and the like filled with the amount to be ingested per meal of drinks of suspended or dissolved amino acids mentioned above, and the like. The dose per meal may be a daily dose mentioned above.

Specific examples thereof include a food intake regulating agent in a unit packaging form for one meal, which generally contains 6 mg-23 g, preferably 10 mg-20 g, more preferably 50 mg-15 g, particularly preferably 60 mg-15 g, of the amino acids of (1)-(3) in total as the amount to be ingested in the unit.

In addition, a food or drink for regulating food intake, which is in a unit packaging form for one meal, and contains not less than 0.06 g of 3 kinds of amino acids of tryptophan, threonine and methionine in total in the unit, wherein the weight ratio of tryptophan, threonine and methionine is 1:0.5-12:0.2-10, is also one embodiment of the present invention.

Furthermore, the above-mentioned food or drink which is free of an amino acid other than tryptophan, threonine and methionine, that is, the food or drink containing only tryptophan, threonine and methionine as amino acids is also one embodiment of the present invention.

Examples thereof include a food intake regulating agent in a unit packaging form for one meal, which generally contains 6 mg-23 g, preferably 10 mg-20 g, more preferably 50 mg-15 g, particularly preferably 60 mg-15 g, of the amino acids of (1)-(4) in total as the amount to be ingested per meal in the unit. Especially, a food intake regulating agent containing 60 mg-2 g is preferable.

In addition, a food or drink for regulating food intake, which is in a unit packaging form for one meal, and contains not less than 0.06 g of 4 kinds of amino acids of tryptophan, threonine, methionine and isoleucine in total in the unit, wherein the weight ratio of tryptophan, threonine, methionine and isoleucine is 1:0.5-12:0.2-10:0.5-12, is also one embodiment of the present invention.

Among these, not more than 5 g, more preferably not more than 3 g, further preferably not more than 2 g, in total of the above-mentioned 4 kinds of amino acids is preferably contained.

Furthermore, the above-mentioned food or drink which is free of an amino acid other than tryptophan, threonine, methionine and isoleucine, that is, the food or drink containing only tryptophan, threonine, methionine and isoleucine as amino acids is also one embodiment of the present invention.

Examples thereof include a food intake regulating agent in a unit packaging form for one meal, which generally contains 6 mg-23 g, preferably 10 mg-20 g, more preferably 50 mg-15 g, particularly preferably 60 mg-15 g, of the amino acids of (1)-(5) in total as the amount to be ingested per meal in the unit.

In addition, a food or drink for regulating food intake, which is in a unit packaging form for one meal, and contains not less than 0.06 g of 5 kinds of amino acids of tryptophan, threonine, methionine, isoleucine and valine in total in the unit, wherein the weight ratio of tryptophan, threonine, methionine, isoleucine and valine is 1:0.5-12:0.2-10:0.5-12: 0.5-15, is also one embodiment of the present invention.

Among these, not more than 5 g, more preferably not more than 3 g, further preferably not more than 2 g, in total of the above-mentioned 5 kinds of amino acids is preferably contained.

Furthermore, the above-mentioned food or drink which is free of an amino acid other than tryptophan, threonine, methionine, isoleucine and valine, that is, the food or drink containing only tryptophan, threonine, methionine, isoleucine and valine as amino acids is also one embodiment of the present invention.

More particularly, a unit packaging form for one meal which contains, as one ingestion amount in the unit, generally (1) 1 mg-9 g, (2) 3 mg-20 g, (3) 2 mg-18 g, (4) 0-20 g, (5) 0-20 g, preferably (1) 2 mg-6 g, (2) 6 mg-18 g, (3) 4 mg-15 g, (4) 6 mg-18 g, (5) 10 mg-18 g, more preferably (1) 8 mg-5 g, (2) 25 mg-15 g, (3) 17 mg-12 g, (4) 25 mg-15 g, (5) 40 mg-16 g can be mentioned.

For a unit packaging form per 10-60 meals, the above-mentioned numerical values can be set to 10- to 60-fold.

In consideration of a food containing other amino acid, the weight (%) of each amino acid in the amino acids contained in a food or drink containing the amino acids of (1)-(3) of the present invention is
iv. tryptophan 0.5%-45%, (2) threonine 1.5%-70%, (3) methionine 1.0%-50%, preferably (1) 3.5%-40%, (2) 5%-65%, (3) 6%-45%, more preferably (1) 5%-33%, (2) 8%-60%, (3) 10%-40%.

In a food or drink containing the amino acids of (1)-(4) of the present invention, the weight (%) of each amino acid in the contained amino acids is
v. tryptophan 0.5%-45%, (2) threonine 1.5%-70%, (3) methionine 1.0%-50%, (4) isoleucine 0.001%-50%, preferably (1) 3.5%-40%, (2) 5%-65%, (3) 6%-45%, (4) 0.001%-45%, more preferably (1) 5%-33%, (2) 8%-60%, (3) 10%-40%, (4) 0.001%-40%.

In a food or drink containing the amino acids of (1)-(5) of the present invention, the weight (%) of each amino acid in the contained amino acids is
vi. tryptophan 0.5%-45%, (2) threonine 1.5%-70%, (3) methionine 1.0%-50%, (4) isoleucine 0.01%-50%, (5) valine 0.001%-60%, preferably (1) 3.5%-40%, (2) 5%-65%, (3) 6%-45%, (4) 0.001%-45%, (5) 0.001%-55%, more preferably (1) 5%-33%, (2) 8%-60%, (3) 10%-40%, (4) 0.001%-40%, (5) 0.001%-50%.

The present invention is explained in more detail in the following by referring to Examples, which do not limit the present invention.

EXAMPLES

The present invention is explained in detail by the following Examples.

[Example 1] Granular Powder Nutrition Composition

In consideration of the optimal effect on food intake adjustment, the nutrition composition shown in Table 1 was formulated, based on which a granular powder product was prepared as the nutrition composition of the present invention. That is, a mixture having the composition of Table 1 was mixed in a compact high speed mixer (NSK-150S, manufactured by OKADA SEIKO CO., LTD.) for 5 min. Thereafter, 2-5 wt % of distilled water was added to the mixture, and the mixture was further kneaded in the mixer for 5 min to give a moist kneaded mixture. The moist kneaded mixture was granulated using an extrusion granulator with a 1.0 mmφ screen, the obtained formed product was dried at 80° C. under normal pressure for 30 min and sieved, and 1.25 g of the granules was filled in an aluminum bag. The whole components of the granular powder nutrition composition of this Example were stable even after one year. In addition, this granular powder nutrition composition could be used by dissolving in warm water and mixing with a nutritional supplement, and could be prepared as an ion drink. Furthermore, it could be further mixed with a spice, salts such as sodium chloride and the like, sodium glutamate, nucleic acid and the like, and added to various foods.

TABLE 1

|  | unit | wt % (weight ratio) |
| --- | --- | --- |
| L-tryptophan | % | 6 (1.0) |
| L-threonine | % | 17 (2.8) |
| L-methionine | % | 12 (2.0) |
| L-isoleucine | % | 18 (3.0) |
| L-valine | % | 27 (4.5) |
| lactose | % | 12 |
| sucrose | % | 8 |
| total amount | % | 100 |

[Example 2] Granular Powder Nutrition Composition

In the same manner as in Example 1 except that a mortar was used instead of the high speed mixer for kneading and a horizontal extruder (manufactured by UMETANI TEKKOUSHO) was used as the extrusion granulator, a granular powder could be obtained.

[Example 3] Jelly-Like Nutrition Composition

In consideration of the optimal effect on food intake adjustment, the nutrition composition shown in Table 2 was formulated, based on which a jelly nutrition composition was prepared as the nutrition composition of the present invention. That is, thickened polysaccharide and water were added to the composition of Table 2, and the mixture was emulsified by mixing and stirring with heating. After cooling, the emulsion was adjusted to pH 3.8, and sterilized by heating at 80° C. for 10 min. 1.25 g was cooled and filled in a pouch. The whole components of the jelly nutrition composition of this Example were stable even after one year.

TABLE 2

|  | unit | wt % (weight ratio) | wt % (weight ratio) |
| --- | --- | --- | --- |
| L-tryptophan | % | 6 (1.0) | 10 (1.0) |
| L-threonine | % | 17 (2.8) | 30 (3.0) |
| L-methionine | % | 12 (2.0) | 19 (1.9) |
| L-isoleucine | % | 18 (3.0) | 22 (2.2) |
| L-valine | % | 27 (4.5) | 0 |
| lactose | % | 12 | 12 |
| sucrose | % | 8 | 7 |
| total amount | % | 100 | 100 |

[Example 4] Liquid Nutrition Composition

In deep consideration of optimal nutrition effect to elderly people, the liquid nutrition composition shown in Table 3 was prepared. The amounts of the starting materials of a liquid product for realizing this are shown in Table 3. Each component and an emulsifier were mixed with water, and an emulsification step was repeated plural times in a high-pressure emulsifier under pressurization at 500-1,000 kg/cm$^2$ to give an emulsion composition. This emulsion composition was filled in an aluminum bag by a general filling machine, and sterilized by a retort sterilizing machine under general conditions. The whole components of the nutrition composition of this Example were stable even after one year. In addition, a thickener was added to the prepared solution, whereby a thickened nutrition composition (1,000-7,000 mPa s) or jelly could be produced. Furthermore, similar production was possible even when the amount of the amino acid to be added was 3-fold. The caloric density of this nutrition composition was 1.6 kcal/ml.

TABLE 3

50 mL (80 kcal)/pack

| component | unit | content/pack (weight ratio) |
|---|---|---|
| protein | g | 0.9 |
| L-tryptophan | g | 0.07 (1.0) |
| L-threonine | g | 0.20 (2.9) |
| L-methionine | g | 0.13 (1.9) |
| L-isoleucine | g | 0.21 (3.0) |
| L-valine | g | 0.30 (4.3) |
| lipid | g | 4.8 |
| middle chain fatty acid | g | 0.7 |
| hydrocarbonate | g | 14.7 |
| carbohydrates | g | 13.2 |
| dietary fiber | g | 1.5 |
| sodium | mg | 88.3 |
| calcium | mg | 35.8 |
| iron | mg | 1.7 |
| phosphorus | mg | 34.6 |
| magnesium | mg | 16.6 |
| potassium | mg | 101.8 |
| copper | mg | 0.01 |
| iodine | μg | 6.4 |
| selenium | μg | 0.9 |
| zinc | mg | 1.9 |
| vitamin A | μg RE *1 | 76.8 |
| vitamin D | μg | 0.3 |
| vitamin E | mg α-TE *2 | 3.4 |
| vitamin K | μg | 7.0 |
| vitamin B$_1$ | mg | 0.1 |
| vitamin B$_2$ | mg | 0.1 |
| niacin | mg NE *3 | 1.2 |
| vitamin B$_6$ | mg | 0.3 |
| folic acid | μg | 25.6 |
| vitamin B$_{12}$ | μg | 0.5 |
| pantothenic acid | mg | 1.0 |
| vitamin C | mg | 8.3 |

*1: retinol equivalent
*2: α-tocopherol reduced quantity
*3: niacin equivalent

[Example 5] Corn Soup Nutrition Composition

In consideration of the optimal nutrition effect of food intake adjustment, the nutrient composition shown in Table 4 was formulated, based on which a corn soup nutrition composition was prepared as the nutrition composition of the present invention. The starting materials shown in Table 4 were mixed, and the mixture was fluidized bed granulated to prepare a powdered corn soup (20 g). Furthermore, consomme soup and pumpkin soup could also be produced similarly.

TABLE 4

| | unit | wt % (weight ratio) | wt % (weight ratio) |
|---|---|---|---|
| L-tryptophan | % | 0.5 (1.0) | 2.2 (1.0) |
| L-threonine | % | 1.0 (2.0) | 6.0 (2.7) |
| L-methionine | % | 0.9 (1.8) | 4.8 (2.2) |
| L-isoleucine | % | 1.0 (2.0) | 5.4 (2.4) |
| L-valine | % | 1.5 (3.0) | 0.0 |
| corn powder | % | 29.4 | 20.2 |
| potato starch | % | 20.6 | 15.0 |
| crushed sugar | % | 7.8 | 7.8 |
| pulverized sodium glutamate | % | 3.6 | 4.9 |
| pulverized sodium chloride | % | 8.2 | 8.2 |
| non-fat dried milk | % | 6.9 | 6.9 |
| fat and oil powder | % | 8.8 | 8.8 |
| lactose | % | 9.8 | 9.8 |
| total amount | % | 100 | 100 |

[Experimental Example 1] Study of Influence of 5 Kinds of Amino Acids on Overeating Model An influence of a particular amino acid in the nutrition composition of the present invention on the control of feed consumption was studied by the following experiment. That is, a 5 wt % casein feed based on standard purified feed AIN-93G (manufactured by Oriental Yeast Co., Ltd.) was produced and fed to 9-week-old male F344 (Fischer) rats. As a result, the food intake amount in 2 weeks after the feed change increased to about 1.3-fold as compared to the rats fed with a 20 wt % casein feed. Using this as an overeating model, an influence of amino acid administration was evaluated.

Using the overeating model, an administration test of amino acid was performed. As the amino acid, total amino acid (A11AA), non-essential amino acid (NEAA), essential amino acid (EAA) or 5 kinds of amino acids (5AA) were added to a 5 wt % casein feed and administered. The compositions and amounts of the amino acids are shown in Table 5. The composition of the amino acid was constituted based on the amino acid composition of the casein protein, and an amount corresponding to 15 wt % casein was added to the feed. The content excluding the amino acid was replaced by cornstarch. The food intake amount in 2 weeks after the feed change was measured.

TABLE 5 amino acid composition (wt % to total amino acid) and amino acid amount per 1 kg feed

| | unit | AllAA | NEAA | EAA | 5AA | weight ratio |
|---|---|---|---|---|---|---|
| L-tryptophan | % | 1.2 | | 2.4 | 6.2 | 1.0 |
| L-threonine | % | 4.1 | | 8.5 | 21.7 | 3.5 |
| L-methionine | % | 2.6 | | 5.4 | 13.9 | 2.2 |
| L-isoleucine | % | 4.7 | | 9.9 | 25.4 | 4.1 |
| L-valine | % | 6.1 | | 12.8 | 32.8 | 5.3 |
| L-leucine | % | 8.7 | | 18.2 | | |
| L-lysine hydrochloride | % | 9.4 | | 19.7 | | |
| L-phenylalanine | % | 4.8 | | 10.1 | | |
| L-histidine | % | 2.7 | | 5.7 | | |
| L-arginine | % | 3.5 | | 7.3 | | |
| L-alanine | % | 2.7 | 5.2 | | | |
| L-asparagine monohydrate | % | 3.8 | 7.3 | | | |
| L-aspartic acid | % | 3.4 | 6.5 | | | |
| L-cystine | % | 0.5 | 1.0 | | | |
| L-glutamine | % | 9.8 | 18.7 | | | |

TABLE 5-continued

| | unit | A11AA | NEAA | EAA | 5AA | weight ratio |
|---|---|---|---|---|---|---|
| L-glutamic acid | % | 9.8 | 18.7 | | | |
| L-glycine | % | 1.7 | 3.3 | | | |
| L-proline | % | 10.0 | 19.1 | | | |
| L-serine | % | 5.4 | 10.3 | | | |
| L-tyrosine | % | 5.1 | 9.9 | | | |
| amount of total amino acid (g/kg) | g/kg | 140.7 | 73.6 | 67.2 | 26.3 | |

FIG. 1 shows an average food intake amount per day in 2 weeks after changing the feed. It was found that overeating can be suppressed by adding an amino acid (A11AA) in an amount corresponding to 15% of amino acid in casein composition to a 5 wt % casein feed. While overeating could not be suppressed by adding only non-essential amino acid moiety of the amino acids (NEAA), overeating was suppressed when essential amino acid (EAA) or 5 kinds of amino acids were added (5AA).

From the above-mentioned test results, it was found that a suppressive effect on overeating was obtained by adding 5 kinds of amino acids at 26.3 g per 1 kg feed. To obtain a similar effect, 140.7 g of total amino acids of the casein composition or 67.2 g of essential amino acid is necessary. Thus, it was found that 5 kinds of amino acids do not require ingestion of many proteins and amino acids, and can regulate feed consumption efficiently with a small amount thereof.

[Experimental Example 2] Study of Influence of 3-5 Kinds of Amino Acids on Overeating Model Using an overeating model, whether the kind of the amino acids can be further reduced from 5 kinds of amino acids that proved effective for suppressing overeating was studied. As the amino acid, 5 kinds of amino acids (5AA) or those excluding one or two kinds were added to a 5 wt % casein feed. The compositions and amounts of the amino acids are shown in Table 6. The composition of the amino acid was constituted based on the amino acid composition of the casein protein, and an amount corresponding to 15 wt % casein was added to the feed. The content excluding the amino acid was replaced by cornstarch. The food intake amount in 2 weeks after the feed change was measured.

Figure 2:
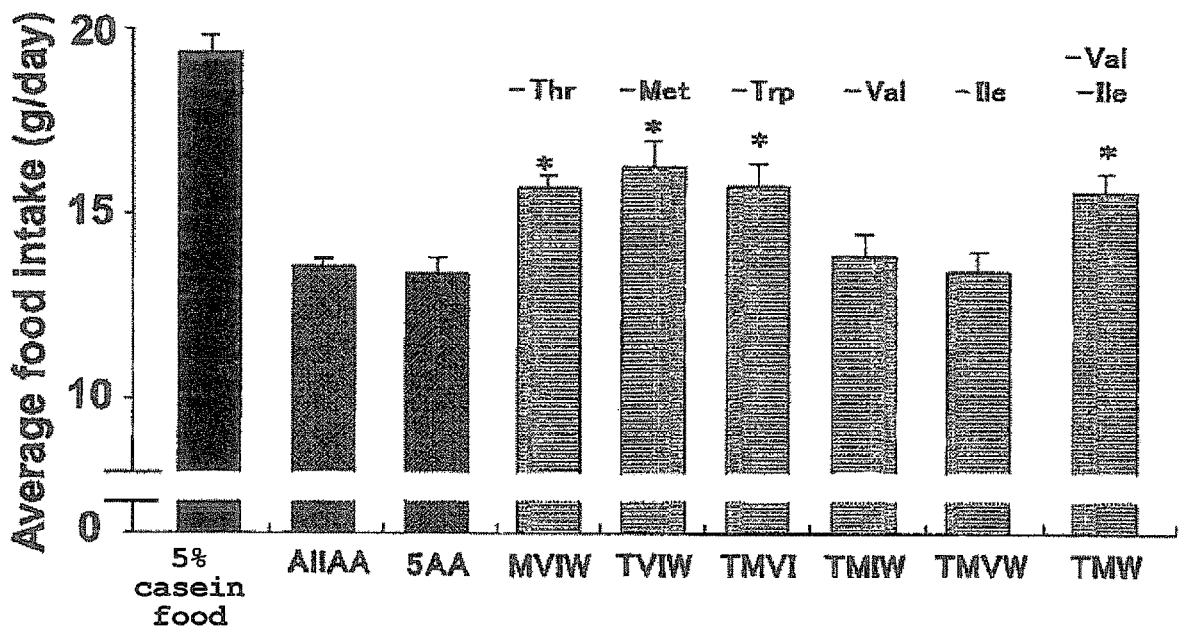
FIG. 2 shows an average food intake per day at 2 weeks after feed exchange. * shows a significant difference (p<0.05) as compared to 5AA.

FIG. 2 shows an average food intake amount per day in 2 weeks after changing the feed. Overeating was suppressed when an amino acid (A11AA) in an amount corresponding to 15% of amino acid in casein composition was added or 5 kinds of amino acids were added (5AA) to a 5 wt % casein feed. Overeating was suppressed even when only one kind of L-valine or L-isoleucine was removed from 5AA. In contrast, when any one kind of L-threonine, L-methionine and L-tryptophan, or two kinds of L-valine and L-isoleucine were removed, suppression of overeating was attenuated. The present test suggests that, L-threonine, L-methionine and L-tryptophan in the 5 kinds of amino acids were essential for a suppressive effect on overeating, and a possibility of maintaining the suppressive effect on overeating even after removing any of L-valine and L-isoleucine was suggested. However, when two kinds of L-valine and L-isoleucine were simultaneously removed, the suppressive effect on overeating was clearly attenuated.

[Experimental Example 3] Study of Influence of 5 Kinds of Amino Acids on Decreased Feed Consumption Model Sequentially, an influence of a particular amino acid in the nutrition composition of the present invention on a decrease in the feed consumption was studied by the following experiment. In this test, 10-week-old male C57BL/6J mouse was used, and raised on a standard purified feed AIN-93G (manufactured by Oriental Yeast Co., Ltd.) in which protein was reduced to 1 wt % casein. As a result, the animal fed with a 1 wt % casein diet showed a decrease of about 70% on day 20 and thereafter as compared to the animal fed with a 20 wt % casein feed. Using this as a decreased food consumption model, an influence of amino acid administration was evaluated.

Using the decreased food consumption model, an administration test of amino acid was performed. As the amino acid, a mixed aqueous solution of essential amino acid (EAA) or 5 kinds of amino acids (5AA) was administered. The compositions and dose of the amino acids are shown in Table 7. The composition of the amino acid was constituted based on the amino acid composition of the casein protein, and administered immediately before the dark period which is a mouse active period, and the food intake amount in 2 hours after the administration was measured.

TABLE 6

| | unit | MVIW | TVIW | TMVI | TMIW | TMVW | TMW | weight ratio |
|---|---|---|---|---|---|---|---|---|
| L-tryptophan | % | 7.9 | 7.2 | | 9.2 | 8.3 | 14.8 | 1 |
| L-threonine | % | | 25.3 | 23.2 | 32.3 | 29.2 | 52.0 | 3.5 |
| L-methionine | % | 17.8 | | 14.8 | 20.7 | 18.6 | 33.2 | 2.2 |
| L-isoleucine | % | 32.5 | 29.5 | 27.1 | 37.8 | | | 4.1 |
| L-valine | % | 41.8 | 38.0 | 34.9 | | 43.9 | | 5.3 |
| amount of total amino acid (g/kg) | g/kg | 20.5 | 22.6 | 24.6 | 17.7 | 19.6 | 11.0 | |

TABLE 7 amino acid composition (wt % to total amino acid) and dose

|  | unit | EAA | 5AA | weight ratio |
|---|---|---|---|---|
| L-tryptophan | % | 3.2 | 7.3 | 1.0 |
| L-threonine | % | 9.3 | 21.5 | 2.9 |
| L-methionine | % | 6.4 | 14.7 | 2.0 |
| L-isoleucine | % | 10.0 | 23.0 | 3.1 |
| L-valine | % | 14.5 | 33.5 | 4.6 |
| L-leucine | % | 20.9 | | |
| L-lysine hydrochloride | % | 17.3 | | |
| L-phenylalanine | % | 11.4 | | |
| L-histidine | % | 7.0 | | |
| dose (g/kg BW) | g/kg BW | 0.30 | 0.13 | |

Figure 3:
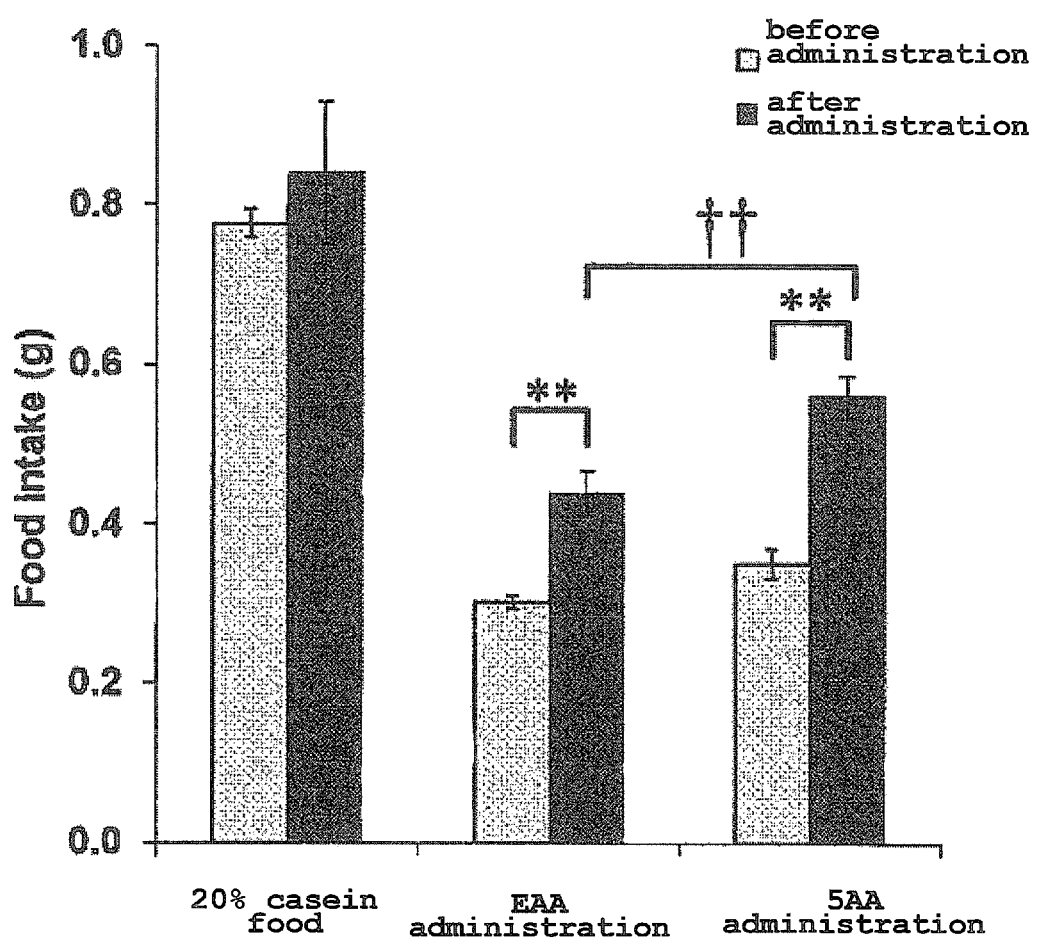
FIG. 3 shows food intake in the dark period for 2 hr before and after administration. ** shows a significant difference (p<0.01) as compared to before administration, †† shows a significant difference (p<0.01) as compared to EAA.

FIG. 3 shows food intake amounts before administration and 2 hr in the dark period after administration. After administration, a significant increase in the food intake amount was found as compared to that before administration; 145% in the essential amino acid administration group (EAA) and 160% in the 5 kinds of amino acids administration group (5AA). Particularly, the 5 kinds of amino acids administration group showed a significant food intake amount increasing effect even when compared to the essential amino acid administration group.

[Experimental Example 4] Study of Influence of Administration of 5 Kinds of Amino Acids Blend Feed on Feed Consumption Decrease Model A food consumption decrease model was fed with a test feed, which was prepared by reducing the protein in standard purified feed AIN-93G (manufactured by Oriental Yeast Co., Ltd.) to give a 1 wt % casein feed, and adding 5 kinds of amino acids at a proportion of 0.2 wt %, for 2 weeks, and a blend feed administration test was performed. The compositions of 5 kinds of amino acids are similar to those in Table 7.

Figure 4:
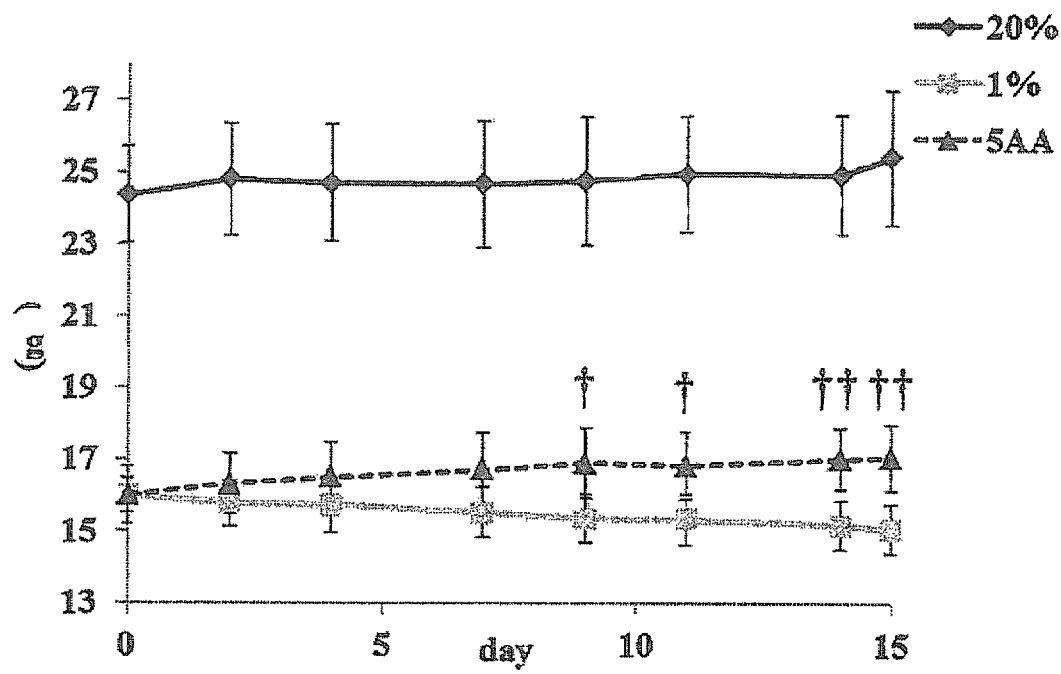
FIG. 4 shows body weight profile in 2 weeks of a blend feed test. † shows a significant difference (p<0.05) as compared to 1% weight casein food group, and †† shows a significant difference (p<0.01) as compared to 1% weight casein food group.
Figure 5:
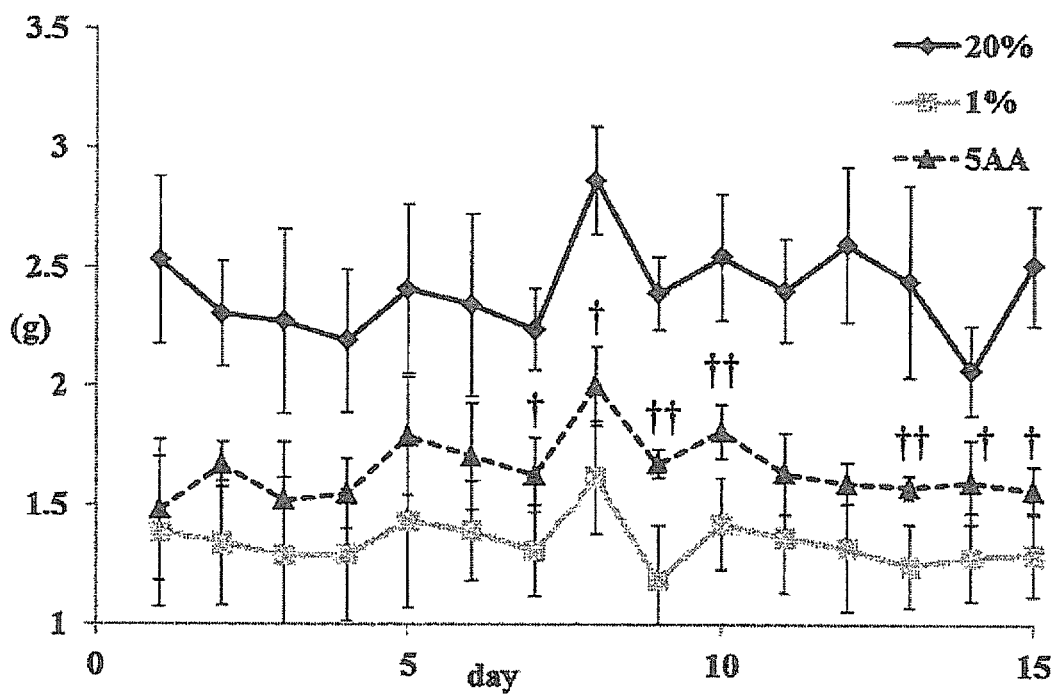
FIG. 5 shows food intake profile in the dark period. † shows a significant difference (p<0.05) as compared to 1% weight casein food group, and †† shows a significant difference (p<0.01) as compared to 1% weight casein food group.

The body weight profile in the blend feed test for 2 weeks is shown in FIG. 4, and the food intake amount profile in the dark period is shown in FIG. 5. Both the body weight and food intake amount of the 5AA addition feed group significantly increased after 7 days from the start of the test feed as compared to the 1 wt % casein food group free of amino acid addition.

Figure 6:
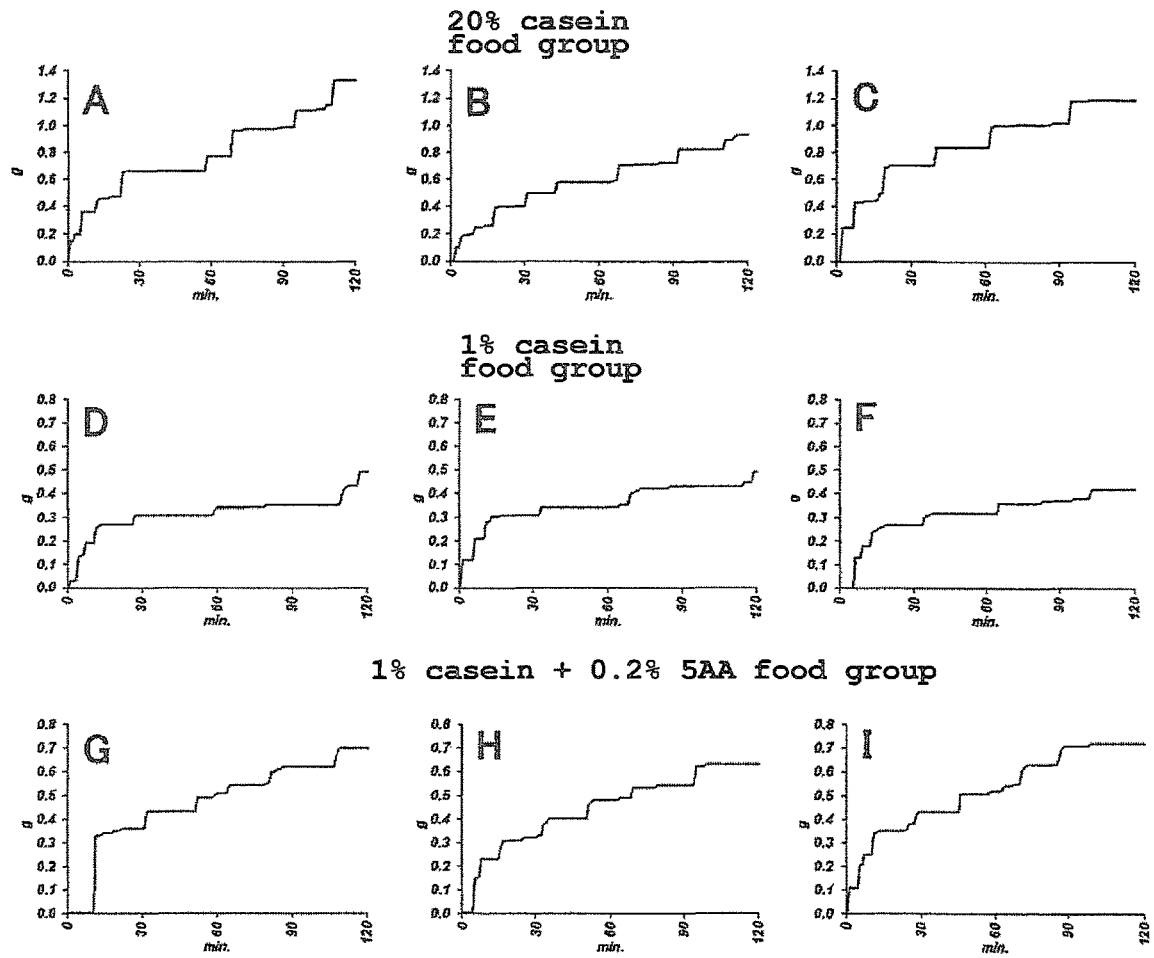
FIG. 6 shows food intake profile in the dark period for 2 hr at 8 days after the start of a blend feed test (3 examples for each group). A, B, C: 20 wt % casein food group, D, E, F: 1 wt % casein food group, G, H, I: 5AA food group.

The food intake amount profiles for 2 hr in the dark period after 8 days from the start of the blend feed test of 3 examples for each group are shown in FIG. 6. For 2 hr in the dark period, the graph showed a flat shape since the food intake amount per one time is small in the 1 wt % casein food group as compared to that of the 20 wt % casein food group measured at the same date and time after the start of the dark period. In contrast, since the food intake amount per one time increased in the 5AA group, the shape of the graph became closer to that of the 20 wt % casein food group.

The meal pattern was analyzed according to the following standard by reference to Neuropsychopharmacology 2003, Vol. 28, pp. 1311-1316.

As for one meal, the conditions of meal size (MS) of not less than 0.01 g and simultaneously postprandial intermeal interval (IMI) of not less than 10 min were satisfied.

Figure 7:
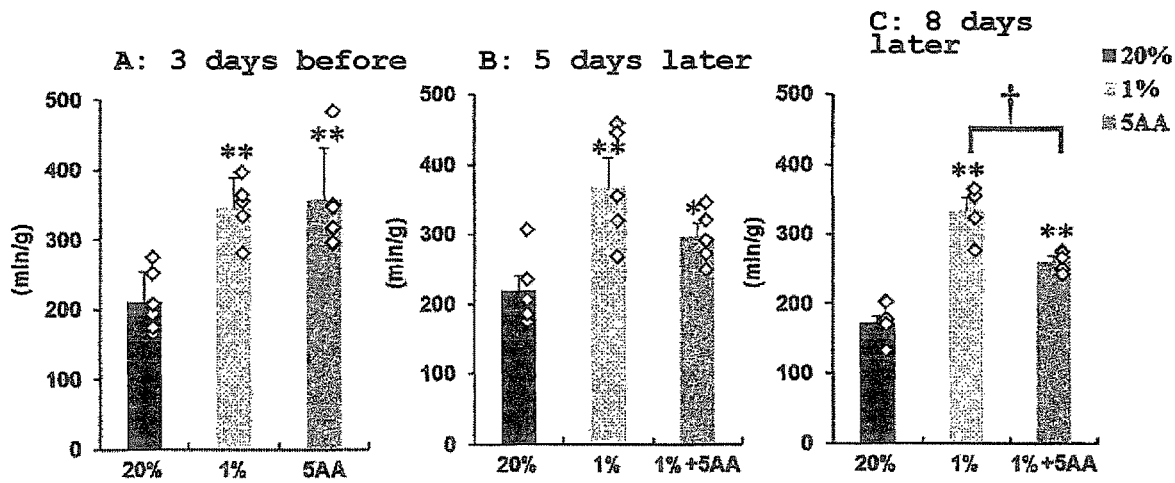
FIG. 7 shows satiety degree in the dark period for 12 hr at 3 days before, 5 days after, and 8 days after the start of a blend feed test. A: 3 days before, B: 5 days after, C: 8 days after. * shows a significant difference (p<0.05) as compared to 20% weight casein food group, ** shows a significant difference (p<0.01) as compared to 20% weight casein food group, † shows a significant difference (p<0.05) as compared to 1% weight casein food group.

The satiety ratio (SR) is calculated as a division of IMI/MS, and increases in response to each of a decrease in MS and an extension of IMI. SR at 3 days before, 5 days after and 8 days after the start of the blend feed test are shown in FIG. 7.

At 3 days before the start of the blend feed test, SR significantly increased in the 1 wt % casein food group and the 5AA group as compared to the 20 wt % casein food group. However, SR of the 5AA group decreased after the start of the blend feed test.

From these results, it was also found that the meal pattern of the 5AA group was closer to that of the 20 wt % casein food group.

Figure 8:
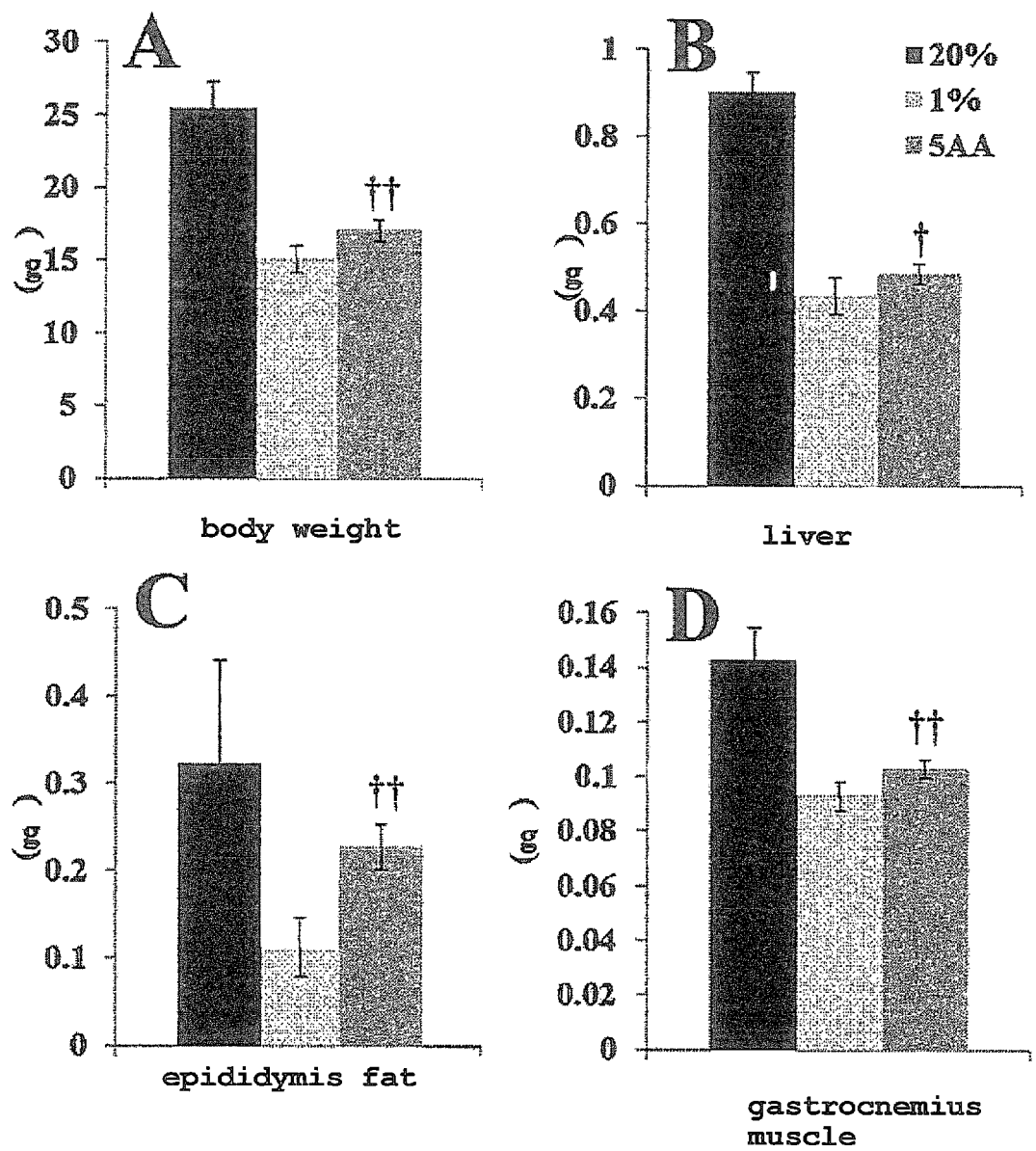
FIG. 8 shows body weight and each organ weight after 2 weeks of a blend feed test. A: body weight, B: liver weight, C: epididymis fat weight, D: gastrocnemius muscle weight. † shows a significant difference (p<0.05) as compared to 1% weight casein food group, and †† shows a significant difference (p<0.01) as compared to 1% weight casein food group.

The body weight and each organ weight after 2 weeks from the blend feed test are shown in FIG. 8. It was shown that all of body weight, liver weight, epididymis fat weight and gastrocnemius muscle weight decreased in the 1 wt % casein food group as compared to those of the 20 wt % casein food group, and were recovered in the 5AA group.

[Experimental Example 5] Study of Effect of Administration 4 Kinds of Amino Acids to in-Home Elderly People Based on the production method of Example 1, granules containing L-tryptophan, L-threonine, L-methionine and L-isoleucine at a weight ratio of 1:2.9:2.0:3.1 were produced (Table 8).

The granules in an amount corresponding to 1 g of a total amount of amino acids were ingested by ten elderly people (2 males, 8 females, average age 79.7±7.7 years old) once per day for 2 months. Inquiring survey of food ingestion frequency and incentive to having a meal before and after the start of amino acid granule ingestion, and meal intake amount and the contents of the meal, and the measurement of body weight were compared.

TABLE 8

|  | unit | wt % (weight ratio) |
|---|---|---|
| L-tryptophan | % | 10.46 (1.0) |
| L-threonine | % | 30.70 (2.9) |
| L-threonine | % | 21.01 (2.0) |
| L-isoleucine | % | 32.89 (3.1) |
| sucrose fatty acid ester | % | 2.85 |
| flavor preparation | % | 0.95 |
| lecithin | % | 1.14 |
| 99.5% alcohol | | — |
| distilled water | | — |
| the total amount | % | 100.00 |

The inquiry used for food ingestion frequency search constituted of 44 questions (in-between snacks, principal food, potatoes, fruits, hypochromic vegetable, deep yellow vegetables, seaweeds, mushrooms, pickles, tofu, nattou, sesami, meat (liver, processed food), fish and shellfish (fish, squid, shrimp, octopus, fishery paste product), chicken egg, milk, cheese, yoghurt, butter•margarine, dressing•mayonnaise, salt-preserved product, deep-fried food, fried food, cooked food, soup, alcohol).

In addition, using the problem solving nutrition system of CORE CREATE SYSTEM, 13 items of ingested nutrients (energy, protein, lipid, hydrocarbonate, calcium, iron, vitamin A, vitamin B1, vitamin B2, vitamin C, vitamin D, dietary fiber, salt content) were converted.

The ingested nutrient amounts converted from the results of the food ingestion frequency search before and after the start of amino acid granule ingestion are shown in Table 9. As a result of comparison between before and after the start of amino acid granule ingestion, the ingested amounts of energy, protein, lipid, vitamin D significantly increased after the amino acid granule ingestion.

TABLE 9 comparison of ingested nutrient amounts before
and after amino acid granule ingestion

|  | before ingestion mean ± S.D. | 2 months after ingestion mean ± S.D. | p value |
|---|---|---|---|
| energy (kcal) | 1591 ± 224.0 | 1764 ± 321.6 | 0.017* |
| protein (g) | 57.5 ± 8.5 | 66.4 ± 11.9 | 0.018* |
| lipid (g) | 47.4 ± 12.7 | 59.4 ± 19.2 | 0.003* |
| hydrocarbonate (g) | 237.0 ± 31.9 | 241.8 ± 45.9 | 0.699 |
| calcium (mg) | 644 ± 152.7 | 639 ± 156.5 | 0.938 |
| iron (mg) | 11.8 ± 3.3 | 11.8 ± 3.4 | 0.972 |
| vitamin A (mg) | 1620 ± 503.8 | 1733 ± 827.7 | 0.688 |
| vitamin B1 (mg) | 1.05 ± 0.2 | 1.14 ± 0.3 | 0.217 |
| vitamin B2 (mg) | 1.26 ± 0.3 | 1.41 ± 0.3 | 0.121 |
| vitamin C (mg) | 213 ± 41.5 | 204 ± 79.2 | 0.612 |
| vitamin D (μg) | 5.3 ± 2.6 | 8.0 ± 2.8 | 0.007* |
| dietary fiber (g) | 22.5 ± 6.0 | 21.0 ± 6.2 | 0.456 |
| salt content (g) | 10.3 ± 1.7 | 10.3 ± 1.6 | 0.972 |

The items of inquiry used for food ingestion frequency search are divided into 6 food groups and shown in Table 10.

TABLE 10

6 basic foods

| food group | | nutritional characteristics |
|---|---|---|
| 1 | fish/meat egg bean/soybean product | protein source |
| 2 | milk/milk product seaweed small fish | calcium source |
| 3 | deep yellow vegetables | vitamin A source |
| 4 | other vegetables fruit | vitamin C source |
| 5 | grains potatoes saccharides | carbohydrate energy source |
| 6 | fats and oils | fat energy source |

The results of food ingestion frequency before and after the start of amino acid granule ingestion, which are divided into food groups, are shown in Table 11. As a result of comparison between before and after the start of amino acid granule ingestion, the ingestion frequency of the foods of group 1 (protein source) significantly increased after the amino acid granule ingestion.

TABLE 11 comparison of ingestion frequency of 6 food groups
before and after amino acid granule ingestion

|  | before ingestion mean ± S.D. | 2 months after ingestion mean ± S.D. | p value |
|---|---|---|---|
| group 1 | 3.4 ± 1.2 | 3.9 ± 1.2 | 0.002* |
| group 2 | 3.7 ± 1.5 | 3.7 ± 1.5 | 0.870 |
| group 3 | 2.7 ± 1.3 | 2.8 ± 1.2 | 0.840 |
| group 4 | 2.7 ± 1.3 | 2.6 ± 1.3 | 0.660 |
| group 5 | 3.0 ± 0.7 | 2.9 ± 1.0 | 0.730 |
| group 6 | 3.9 ± 1.6 | 4.0 ± 1.3 | 0.680 |

The results of meal intake amount before and after the start of amino acid granule ingestion are shown in Table 12. As a result of comparison between before and after the start of amino acid granule ingestion, the intake amount of the main dish significantly increased after the amino acid granule ingestion.

TABLE 12 comparison of meal intake amount before and
after amino acid granule ingestion

| category of meal (g) | before ingestion mean ± S.D. | 2 months after ingestion mean ± S.D. | p value |
|---|---|---|---|
| principal food | 149 ± 34.7 | 141 ± 36.2 | 0.051 |
| main dish | 145 ± 39.6 | 194 ± 42.7 | 0.003* |
| side dish(1) | 44 ± 7.8 | 65 ± 30.5 | 0.070 |
| side dish(2) | 78 ± 41.7 | 85 ± 44.9 | 0.580 |
| side dish(3) | 50 ± 11.5 | 52 ± 31.1 | 0.820 |

The search results relating to the manner of taking meals before and after the start of amino acid granule ingestion are shown in Table 13. The search was performed according to the following evaluation criteria, scored and the mean was calculated.

"incentive for taking meal"

eat willingly: 3 points eat when prompted: 2 point no intention to eat: 1 point.

"content of meal"

eat in well-balanced manner: 3 points avoid particular food: 2 points concentrated on eating one dish: 1 point.

As a result of comparison between before and after the start of amino acid granule ingestion, persons who ate only when prompted significantly changed to eat willingly after the amino acid granule ingestion. In addition, persons who were concentrated on eating one dish or avoided particular food came to eat in a well-balanced manner.

TABLE 13 comparison of manners of taking meals
before and after amino acid granule intake

|  | item | before intake n | mean ± S.D. | 2 months after intake n | mean ± S.D. | P value |
|---|---|---|---|---|---|---|
| incentive for meal | eat willingly | 4 | 2.4 ± 0.5 | 9 | 2.9 ± 0.3 | 0.015* |
|  | eat when prompted | 6 |  | 1 |  |  |
|  | no intention to eat | 0 |  | 0 |  |  |
| content of meal | eat in well-balanced manner | 8 |  | 10 |  |  |
|  | avoid particular food | 1 | 2.4 ± 0.8 | 0 | 3.0 ± 0.0 | 0.096 |
|  | concentrated on eating one dish | 2 |  | 0 |  |  |

The body weights before and after the start of amino acid granule ingestion are shown in Table 14. As a result of comparison between before and after the start of amino acid granule ingestion, a significant increase in the body weight was observed after the amino acid granule ingestion.

TABLE 14 comparison of body weight before and after
amino acid granule ingestion

|  | before ingestion mean ± S.D. | 2 months after ingestion mean ± S.D. | p value |
|---|---|---|---|
| age (years old) | 79.7 ± 7.7 | — | — |
| body weight (kg) | 45.0 ± 6.6 | 46.0 ± 6.9 | 0.027* |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of regulating food intake in a subject in need thereof, wherein said subject suffers from a reduction in appetite or suffers from undernutrition due to a reduction in appetite or wherein said subject suffers from overeating or a lifestyle-related disease caused by overeating, comprising administering a composition to said subject comprising, by weight percent:
    a) 3.5% to 40% tryptophan,
    b) 5% to 65% threonine,
    c) 6% to 45% methionine, and
    d) not more than 20% of isoleucine; and
    wherein the composition does not contain any amino acid other than tryptophan, threonine, methionine and isoleucine.

2. The method according to claim 1, wherein the composition does not contain any amino acid other than tryptophan, threonine and methionine.

3. The method according to claim 1, wherein the weight ratio of tryptophan, threonine and methionine is 1:0.5-12:0.2-10.

4. The method according to claim 1, wherein the composition further comprises isoleucine.

5. The method according to claim 4, wherein the weight ratio of tryptophan, threonine, methionine and isoleucine is 1:0.5-12:0.2-10:0.5-12.

6. The method according to claim 1, wherein the composition is in a unit packaging form for one meal and comprises, in the unit, not less than 0.06 g of amino acid to be ingested for one meal as an active ingredient.

7. The method according to claim 1, wherein the reduction in appetite is caused by a condition selected from the group consisting of aging, cancer, inflammation, decreased function of digestive organ, cardiac failure, renopathy, hepatic diseases, autoimmune disorder, lung disease, hypothyroidism, encephalopathy, anorexia nervosa, depression, dementia, Alzheimer's disease, chemotherapeutic agent, antibiotic, trauma after surgery, lack of ghrelin secretion, lack of ghrelin action, psychological stress, physical stress, irregular lifestyle habit, unbalanced diet, and combinations thereof.

8. The method according to claim 1, which is for the prophylaxis or improvement of overeating or a lifestyle-related disease caused by overeating.

9. The method according to claim 8, wherein the overeating is caused by psychological stress, physical stress, bulimia nervosa, depression, irregular lifestyle habit or low-protein diet.

10. A method of regulating food intake of a subject in need thereof, wherein said subject suffers from a reduction in appetite or suffers from undernutrition due to a reduction in appetite, comprising administering a food or drink to said subject, wherein said food or drink is in a unit packaging form for one meal, and wherein said unit packaging form comprises not less than 0.06 g of tryptophan, threonine and methionine, wherein the weight ratio of tryptophan, threonine and methionine is 1:0.5-12:0.2-10, wherein said food or drink comprises, by weight percent:
    a) 3.5% to 40% tryptophan,
    b) 5% to 65% threonine, and
    c) 6% to 45% methionine; and
    wherein the food or drink comprises not more than 20% of isoleucine;
    wherein the food or drink does not contain any amino acid other than tryptophan, threonine, methionine and isoleucine.

11. The method according to claim 10, wherein the food or drink is free of an amino acid other than tryptophan, threonine and methionine.

12. A method of regulating food intake of a subject in need thereof, wherein said subject suffers from a reduction in appetite or suffers from undernutrition due to a reduction in appetite, comprising administering a food or drink to said subject, wherein said food or drink is in a unit packaging form for one meal, and wherein said unit packaging form comprises not less than 0.06 g of tryptophan, threonine, methionine and isoleucine, wherein the weight ratio of tryptophan, threonine, methionine and isoleucine is 1:0.5-12:0.2-10:0.5 12, wherein said food or drink comprises, by weight percent:
    (a) 3.5%-40% tryptophan,
    (b) 5%-65% threonine,
    (c) 6%-45% methionine, and
    (d) 0.001%-45% isoleucine; and
    wherein the food or drink does not contain any amino acid other than tryptophan, threonine, methionine and isoleucine.

13. A method of regulating food intake in a subject in need thereof, wherein said subject suffers from a reduction in appetite or suffers from undernutrition due to a reduction in appetite, comprising administering a food or drink to said subject which is in a unit packaging form for one meal, and wherein said unit packaging form comprises not less than 0.06 g of tryptophan, threonine, methionine, and isoleucine, wherein the weight ratio of tryptophan, threonine, methionine, and isoleucine is 1:0.5-12:0.2-10:-0.5-12, wherein the food or drink is free of an amino acid other than tryptophan, threonine, methionine and isoleucine.

14. A method of regulating food intake in a subject in need thereof, wherein the subject is elderly, said method comprising administering a composition to said subject comprising by weight percent:
    a) 5% to 33% tryptophan,
    b) 8% to 60% threonine,
    c) 10% to 40% methionine, and
    d) not more than 20% of isoleucine;

wherein the composition does not contain any amino acid other than tryptophan, threonine, methionine and isoleucine.

\* \* \* \* \*